United States Patent [19]

Gates et al.

[11] 4,123,379
[45] Oct. 31, 1978

[54] PRODUCTION OF VERY STRONGLY ACIDIC SOLIDS FOR HYDROCARBON CONVERSIONS

[75] Inventors: Bruce C. Gates, Newark, Del.; Vincent L. Magnotta, Whitehall, Pa.; George C. A. Schuit, Neunen, Netherlands

[73] Assignee: University of Delaware, Newark, Del.

[21] Appl. No.: 793,780

[22] Filed: May 4, 1977

[51] Int. Cl.$^2$ .................................................. B01J 31/10
[52] U.S. Cl. .................................. 252/184; 252/429 R; 252/434; 252/436; 260/671 C; 260/683.53; 260/683.75; 208/117
[58] Field of Search ............... 252/429 R, 436, 434, 252/184

[56] References Cited

U.S. PATENT DOCUMENTS

| | | | |
|---|---|---|---|
| 2,842,605 | 7/1958 | Appell | 252/436 X |
| 3,385,797 | 5/1968 | Block et al. | 252/436 X |
| 3,413,362 | 11/1968 | Otaku | 252/436 X |
| 3,708,553 | 1/1973 | Olah | 252/429 X |
| 3,960,764 | 6/1976 | Bernard et al. | 252/429 R |
| 3,965,039 | 6/1976 | Chaplits et al. | 252/436 X |
| 3,984,352 | 10/1976 | Rodewald | 252/429 X |

*Primary Examiner*—Patrick Garvin

[57] ABSTRACT

Solids have been prepared having very strongly acidic properties for hydrocarbon reactions. The solids are synthesized from anhydrous AlCl$_3$ and a solid Brønsted acid.

7 Claims, No Drawings

PRODUCTION OF VERY STRONGLY ACIDIC SOLIDS FOR HYDROCARBON CONVERSIONS

BACKGROUND OF THE INVENTION

The present invention relates to the preparation of very strong solid acids and to processes for hydrocarbon conversion reactions employing such very strong solid acids as catalysts.

The strongest acid solutions known are combinations of Brønsted and Lewis acids such as hydrogen flouride (HF) and antimony pentaflouride (SbF$_5$). These "superacids" are highly active catalysts for hydrocarbon reactions proceeding through carbonium ion intermediates, but they have the processing disadvantages of being corrosive and difficult to separate from reaction products.

U.S. Pats. No. 3,855,342, 3,855,343, 3,862,258, and 3,879,489 describe processes for preparing and applying hydrocarbon alkylation catalyts from macroporous sulfonic acid ion-exchange resins such as Amberlyst 15 and a Lewis acid, boron triflouride (BF$_3$). These catalysts have the disadvantage of requiring a constant recycle of boron triflouride, a gas at ambient conditions, which is noxious and difficult to handle safely. They have the further disadvantage of requiring addition of hydrogen fluoride for activity maintenance, and this compound is also noxious and difficult to handle safely.

U.S. Pat. No. 3,975,299 describes processes for preparing hydrocarbon alkylation, isomerization, and/or cracking catalysts from sulfonated or flourided aluminum oxide and a Lewis acid, antimony pentafluoride. These catalysts have the disadvantage of requiring antimony pentafluoride, a chemical which is expensive, corrosive, noxious, and difficult to handle. They have the further disadvantage of requiring addition of hydrogen fluoride to compensate for any hydrogen fluoride lost from the catalyst during operation.

It is the object of the present invention to prepare a solid catalyst having superacid properties — analogous to those of the solution catalysts — but lacking the processing disadvantages attributed to such solution catalysts. It is the further objective of present invention to prepare a solid catalyst having these superacid properties and not containing any fluorine, a component which generally leads to processing problems related to handling and safety.

SUMMARY OF THE INVENTION

The present invention provides very strongly acidic solids prepared from a macroporous sulfonic acid ion-exchange resin, such as Amberlyst 15, Amberlyst XN-1005, Amberlyst XN-1010 and Amberlyst XN-1011 (available from Rohm and Haas Company) in the hydrogen form, and the Lewis acid aluminum trichloride. (Other solid Brønsted acids, such as those formed from aluminum oxide and chlorosulfonic acid or from silicon dioxide and chlorosulfonic acid can also be applied.) The solid acids prepared according to this invention incorporate a complex formed from nearly anhydrous sulfonic acid groups and nearly anhydrous aluminum trichloride. The solid acid can be reused to effect hydrocarbon conversion reactions without necessity for recycling the Lewis acid. The Lewis acid used in this invention (AlCl$_3$) is particularly advantageous since it is relatively inexpensive, is a solid at ambient conditions, and is widely applied in industrial processing as a catalyst.

Hydrogen chloride may be added to a hydrocarbon reactant to compensate for any hydrogen chloride lost from the solid acid during the hydrocarbon conversion processes. The hydrogen chloride may be supposed to promote or regenerate the solid acid catalyst, but this supposition is in no way meant to limit the invention.

The discovery that aluminum trichloride forms a complex with sulfonic acid groups attached to a solid, in which the components are chemically bonded together, is new and surprising. Heretofore, there has been no evidence showing that a Lewis acid can form a unique complex with attached sulfonic acid groups. It has been found that substantially anhydrous sulfonic acid groups react with substantially anhydrous aluminum trichloride to form hydrogen chloride and solid-attached groups which incorporate sulfur, aluminum and chlorine in the atomic ratio equal to or nearly equal to 2:1:2.

The invention described here is surprising in that the solid acid formed from substantially anhydrous sulfonic acid ion-exchange resin and aluminum trichloride has approximately the same hydrocarbon conversion activity as the solid acid formed from sulfonated or flourided aluminum oxide and antimony pentafluoride. The result is especially surprising because a combination of antimony pentafluoride with a Brønsted acid has generally been found to be a stronger acid and a more active hydrocarbon conversion catalyst than a combination of aluminum trichloride with a Brønsted acid.

The solid acids prepared according to the present invention can be applied in hydrocarbon conversion processes requiring very strong acids. These processes include but are not restricted to isomerization of paraffins (e.g., isomerization of n-butane and isomerization of n-pentane), alkylation of aromatics (e.g., the conversion of benzene and ethylene into ethylbenzene), alkylation of paraffins (e.g., the alkylation of isobutane with propylene), and the cracking of paraffins and of alkylaromatics. These reactions can also be carried out in the presence of reactant mixtures, such as those derived from petroleum refinery streams.

The following example illustrates but in no way limit the practice of this invention:

EXAMPLE 1

A solid superacid was synthesized from anhydrous AlCl$_3$ and a solid polymeric Brønsted acid, macroporous beads of sulfonated poly(styrene-divinylbenzene) (Amberlyst 15, Rohm and Haas). The beads (previously dried under vacuum at about 120° C) were contacted in a fixed-bed reactor at 115° C with a stream of dry nitrogen (N$_2$) containing AlCl$_3$ vapors. (These beads are referred to as bone dry.) The Lewis acid (AlCl$_3$) formed a complex with the sulfonated polymer, liberating HCl. The resulting material had a Cl:Al atomic ratio of approximately 2:1 and an Al:S atomic ratio of approximately 1:2 as determined by analysis of digested samples. The Al and Cl were dispersed uniformly throughout each polymer bead on a microscale (about 1 μm) determined by electron microprobe X-ray analysis.

The character of the polymer beads in hydrocarbon conversion reactions was studied with a steady-state flow reactor operated nearly isothermally at 1 atm and temperatures between 70° and 145° C. The flow distribution was essentially uniform (corresponding to piston flow), and mass transfer effects in the fluid phase were absent. The gas-phase reaction products flowed directly into the sampling valve of a gas chromatograph/mass spectrometer system and were analyzed periodically during an experiment.

The isomerization reaction n-butane → isobutane was approximately first order in reactant partial pressure, and the initial rate was best represented by $$r_i = k_a p_b$$

where $k_a = 0.15 \exp[-8300/RT]$ g moles/(min gram of catalyst atm of n-butane)

$P_b$ = partial pressure of n-butane in atm $R$ = the gas constant; $T$ = absolute temperature, °K between 70° and 106° C and at 1 atm total pressure. The reaction of n-hexane gave cracking products (n-butane, isobutane, n-pentane, isopentane) as well as isomerization products (branched hexanes).

It is apparent that changes and modifications may be made without departing from the invention in its broader aspects. The aim of the appended claims, therefore, is to cover all such changes and modifications as fall within the true spirit and scope of the invention.

We claim:

1. A process for production of a very strongly acidic solid which comprises reacting aluminum trichloride with the sulfonic acid groups of a porous solid having sulfonic acid groups and ion-exchange properties, to produce hydrogen chloride and a solid acidic compound having a sulfur to aluminum to chlorine atomic ratio of about 2:1:2 in the reacted groups.

2. A process according to claim 1 in which vapors of aluminum trichloride substantially free of water are brought in contact with a macroporous solid sulfonated poly(styrene-divinylbenzene) ion-exchange resin in the H+form, which is substantially free of water.

3. A process for the production of a very strong solid acid suitable for use in hydrocarbon conversion reactions, which comprises of reacting aluminum trichloride (A) with a macroporous solid (B) containing sulfonic acid groups at temperatures in the range of −50° to 200° C under anhydrous conditions.

4. A process according to claim 3 wherein the solid (B) containing sulfonic acid groups is sulfonated poly(styrene-divinylbenzene) ion-exchange resin and the reaction results in the formation of a solid complex and in the evolution of HCl.

5. The process according to claim 3, wherein (B) has a fraction of its total sulfonic acid groups partially neutralized (or present in the salt form) with the remaining fraction in the hydrogen form.

6. The process according to claim 3 where (B) is entirely in the H+ form.

7. The process according to claim 5 wherein the neutralized form is sodium sulfonate.

* * * * *